United States Patent [19]

Palomo Coll et al.

[11] 4,230,849

[45] Oct. 28, 1980

[54] PROCESS FOR THE ACTIVATION OF CARBOXYLIC ACIDS

[75] Inventors: Antonio L. Palomo Coll; Jose Diago Meseguer, both of Barcelona, Spain

[73] Assignee: Antibioticos, S.A., Spain

[21] Appl. No.: 53,804

[22] Filed: Jul. 2, 1979

[51] Int. Cl.[2] .................. C07D 499/00; C07D 501/02
[52] U.S. Cl. .................................. 544/28; 260/239.1; 260/465.2; 548/111; 548/248; 548/253; 549/79; 560/109; 562/455
[58] Field of Search ...................... 260/239.1; 544/28

[56] References Cited

U.S. PATENT DOCUMENTS 4,035,352   7/1977   Verwij et al. .................... 544/28

*Primary Examiner*—Jose Tovar
*Assistant Examiner*—James H. Turnipseed
*Attorney, Agent, or Firm*—McGlew and Tuttle

[57] ABSTRACT

A process for the activation of carboxylic acids which is useful for the subsequent conversion of said carboxylic acids into their corresponding amides or esters, based on reacting a 2-oxazolidinone with phosphorus pentachloride and subsequent addition of a salt of the carboxylic acid to be activated.

4 Claims, No Drawings

PROCESS FOR THE ACTIVATION OF CARBOXYLIC ACIDS

FIELD OF THE INVENTION

The invention relates to a process for the activation of carboxylic acids which is useful for the subsequent conversion of said carboxylic acids into their corresponding amides or esters.

SUMMARY OF THE INVENTION

The invention is directed to a process for the activation of carboxylic acids, useful for the subsequent conversion of the carboxylic acids into their corresponding esters or amides, which includes the steps of
(a) reacting one equivalent of a 2-oxazolidinone of the general formula

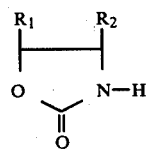

wherein $R_1$ and $R_2$ are selected from the group consisting of hydrogen and alkyl groups having from one to four carbon atoms, with a solvent with at least one-half equivalent of phosphorus pentachloride at temperatures from $-15°$ C. to $+100°$ C. to yield P-trichlorinated N,N'-bis-3(oxazolydinyl-2-one) phosphoranes of the formula

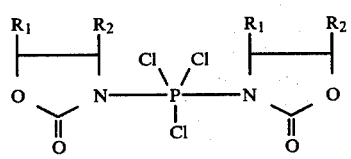

where $R_1$ and $R_2$ are likewise selected from a group consisting of hydrogen and alkyl groups having from one to four carbon atoms; (b) then adding a salt of the carboxylic acid to be activated, to obtain an activation reaction mixture; and treating the resulting activation reaction mixture with one of a compound of the group comprising the compounds having an amine function and the compounds having a hydroxyl function, to yield respectively an amide or an ester.

In accordance with a preferred embodiment of the process the $R_1$ and $R_2$ atoms are hydrogen and the carboxylic acid salt is a tertiary organic base salt. The solvent is preferably selected from the group consisting of methylene chloride, chloroform, nitromethane and acetonitrile either alone or in combination.

DETAILED DESCRIPTION

The process is based on the reaction of said acids with P-trichlorinated N,N'-bis-3(oxazolydinyl-2-one) phosphoranes.

These new phosphorus compounds respond to the following general formula

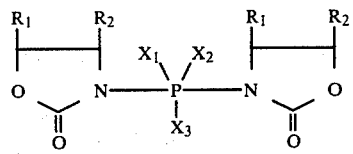

in which $R_1$ and $R_2$ may be atoms of hydrogen or alkyl groups having from one to four carbon atoms and $X_1$, $X_2$ and $X_3$ are preferably chlorine or any substituent introduced by nucleophilic substitution thereof, such as: bromine, cyano, iodine, dimethylformamide, dimethylacetamide, etc. When $X_1=X_2=X_3=Cl$, the compounds respond to the following general formula:

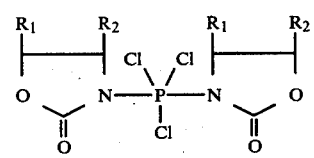

in which $R_1$ and $R_2$ are as defined hereinabove.

In order to simplify the notation of the 2-oxazolidinone groups, they will be abbreviated with the letters OXA, the compounds of the general formula Ia, object of the invention, derived from the general formula I, being represented by the following expression to which reference may be made:

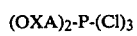

$(OXA)_2\text{-P-}(Cl)_3$

The process of the invention is characterised fundamentally by comprising the following steps:
(a) reacting one equivalent of a 2-oxazolidinone of the general formula

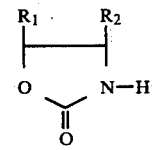

in which $R_1$ and $R_2$ are a group selected from among hydrogen and alkyl groups having from one to four carbon atoms, in an inert solvent with at least one half equivalent of phosphorus pentachloride, at a temperature lying between $-15°$ C. and $+100°$ C., to yield P-trichlorinated N,N'-bis-3(oxazolydinyl-2-one) phosphoranes of the formula

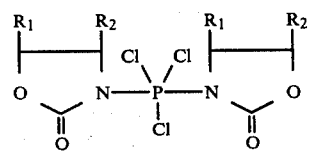

in which $R_1$ and $R_2$ are likewise a group selected from among hydrogen and alkyl groups having from one to four carbon atoms;
(b) adding thereafter a salt of the carboxylic acid to be activated, and
(c) treating the mixture resulting from the activation reaction with a compound of the group comprising compounds with an amine function and compounds with hydroxyl function, to produce an amide or an ester, respectively.

According to a further feature of the invention, $R_1$ and $R_2$ are hydrogen and the carboxylic acid salt is a tertiary organic base salt.

According to yet a further feature of the invention, $R_1$ and $R_2$ are hydrogen; the salt of the carboxylic acid to be activated is a triethylamine salt; and the compound with amine function is selected from among the group including 6-aminopenicillanic acid, 7-aminocephalosporanic acid, 7-aminodesacetoxycephalosporanic acid, 3-substituted 7-amino-$\Delta^3$-cephem-4-carboxylic acid and their corresponding esters.

Preferably, according to the invention, one of the compounds from the group comprising methylene chloride, chloroform, nitromethane and acetonitrile is used as inert solvent, either alone, or in combination.

The interest of these new formula I compounds is based on the fact that their surprising capacity to activate the carboxylic acid and amine functions has just been discovered and they are, therefore, valuable reactant reagents for the purpose of synthesis in industrial processes, an example thereof being the fields of penicillins, cephalosporins, esters of therapeutical value in human and veterinary medicine, and the like.

The family of formula I compounds is prepared in accordance with the sequence shown in Scheme A via two alternative routes, differing from one another in the isolation of the N-trichlorophosphonium-2-oxazolidinone or the direct use with two moles of OXA for one of phosphorus pentachloride.

SCHEME A

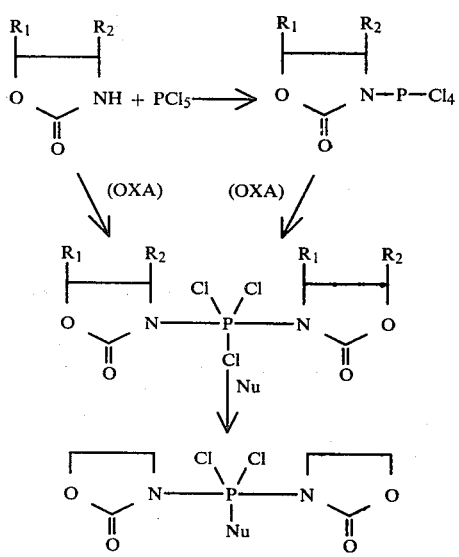

where Nu is a nucleophilic substituent.

One practical way of preparing $(OXA)_2$-P-$(Cl)_3$ comprises reacting a solution of two equivalents of 2-oxazolidinone with one mole of phosphorus pentachloride in an inert solvent, conducting the reaction at room temperature (20°–25° C.) for 24 hours. A particularly appropriate solvent is methylene chloride. Thereafter, the solvent is driven off at reduced pressure to give $(OXA)_2$-P-$(Cl)_3$ with a virtually quantitative yield. In all cases, it is advisable to operate under strictly anhydrous conditions.

In view of the characteristics of the formula I compounds, their "in situ" preparation is recommended.

All these compounds are potential, highly effective reactants, the results of which are reflected in Scheme B. To facilitate the understanding of the matter, this Scheme will be limited to the $(OXA)_2$-P-$(Cl)_3$ of formula Ia, although the results given here are extrapolatable to the remaining formula I compounds.

SCHEME B (a) Reaction with carboxylic acids

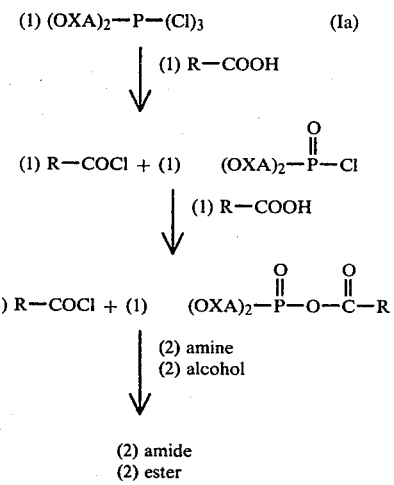

the Figures in brackets () indicate the number of reacting or resulting equivalents.

In certain cases, the formation of the $\Delta_2$ ester of oxazolidinone, also a reactive compound (Spanish Pat. No. 444.470) is detected.

If one chlorine atom in the $(OXA)_2$-P-$(Cl)_3$ is substituted by a dimethylformamide type nucleophilic substitutent, the second stage is made impossible and constitutes a new process for the preparation of acid chlorides.

(b) Reaction with amines

Amides may also be prepared by previously activating the amine function and then adding the carboxylic acid. The reaction may possibly take place through the formation of a —P=N—. In this case, the yields are inferior to those obtained in (a).

To sum up, it may be said that it is possible to activate 2 moles of carboxylic acid, one in the form of acid chloride and the other in the form of acyloxyphosphoramide, with one mole of formula Ia compound.

One of the desirable ways of conducting the process in practice, consists of adding a solution of the triethylamine salt of the carboxylic acid over a suspension containing the compound to be acylated with triethylamine, which acts as acceptor of the protons released.

It has been confirmed that for the object of the invention no limitations or exceptions for the reaction between a carboxylic acid salt and $(OXA)_2$-P-$(Cl)_3$, the following compounds having shown themselves to be usable: 2-thienylacetic acid, 3-thienylacetic acid, cyanacetic acid, 4-pyridinmercaptoacetic acid, 1-(H)-tetrazolylacetic acid, alpha-formyloxyphenylacetic acid, alpha-methoxyimino-2-furylacetic acid, trifluoromethylmercaptoacetic acid, mandilic acid, monophenyl phenylmalonate, mono-5-indamyl phenylmalonate, alpha-azidophenyl acetic acid, 3(2-chlorophenyl)-5-methyl-isoxazolyl-4-carboxylic acid, 3(2,6-dichlorophenyl)-5-methyl-isoxazolyl-4-carboxylic acid, 3(2,6-chlorofluorophenyl)-5-methyl-isoxazolyl-4-carboxylic acid, phenylisoxazolylcarboxylic acid, cyclohexadinylacetic acid, methoxyacetic acid, 4-methyl-1,2,5-oxadiazolyl-3-acetic acid, methylmercaptoacetic acid, alpha-sulphophenylacetic acid, monophenyl 2-thienylmalonate, cyanomethylmercaptoacetic acid, alpha-sulphoisobutoxyphenylacetic acid. In general, acids with an aromatic ring, such as phenyl, naphthyl, tolyl, xylyl, mesityl or heterocyclic groups with one or various heteroatoms such as furane, thiophen, pyrrol, pyrazole, oxadiazole, thiatriazole, imidazole, triazole, thiazole, isodiazole, oxazole, isoxazole, thiadiazole, oxatriazole, tetrazole, pyridine, pyrazine, pyrimidine, pyridazine, benzothiophen, benzofurane, indole, indazole, benzoimidazole, benzothiazole, benzothiadiazole, benzoxazole, quinoline, isoquinoline, quinoxaline, quinazoline, imidazolidine, among others, may be used. The aliphatic, aromatic, heterocyclic residue of these acids may support one or several substituents such as, for example, the halogens, hydroxy, mercapto, carboxyl, alkyl, alkoxy, alkylthio, nitro, sulfo, alkylamino, dialkylamino, cyano, arylcarbonyloxy, arylalkanoyloxy. When the substituents are hydroxy, carboxy and amino, they have a protector group which is eliminated by applying the usual methods.

The preferred organic bases are the tertiary bases which may also be used in the form of salts of weak acids, such a pivalic acid or 2-ethylhexanoic acid, of triethylamine, tributylamine, tripropylamine, picolines, lutidines, cholidines, quinoleins, dimethylaniline and diethylaniline. Nevertheless, the low industrial cost ones are chosen which are easy to eliminate so as to facilitate the isolation of the pure amide or ester.

The amino function compounds which are useful for the invention have not shown any limitations, both with the sterically hindered ones and with those of lower basicity belonging to the aromatic series. As was to be expected, there have been no difficulties with the aliphatic ones and in particular the heterobicyclic ones such as the 6-aminopenicillanic acids (6-APA) and the 7-aminocephalosporanic acids (7-ACA) are of great interest. In these cases, the carboxyl function is found in the form of salt of triethylamine, diethylamine, morpholine and dicyclohexylamine, or as a silyl, benzyl, phenacyl, phthalidic, trichloroethyl ester or aldehyde gem-hydroxyl semi-esters, namely, gem-diacyloxy derivative of aldehydes.

The C-3′ substituents of the 7-aminocephalosporanic acids may be selected from among the group comprising, methyl, acyloxymethyl, alkoxymethyl, formyl, azidomethyl, chloromethyl, formylidene alkyl amino, 5-tertbutoxycarbonylaminomethyl-1,3,4-thiadiazolyl-2-mercaptomethyl, 5-aminomethyl-1,3,4-thiadiazolyl-2-mercaptomethyl, 5(3-methylureidomethyl)-1,3,4-thiadiazolyl-2-mercaptomethyl, carbamoyloxymethyl alpha-methoxy-p-sulphoxy-cinnamoyloxymethyl chlorine and 1-sulphomethyltetrazolyl-5-mercaptomethyl, among other similar heterocyclic groups such as pyridiminomethyl and pyrimidiniummethyl.

The amino function may be linked with a nitrogen atom with or without substituents, in the case of hydrazine, phenylhydrazine and the like, with the process following under identical conditions.

The combination with the $(OXA)_2P-(Cl)_3$ is conducted in an inert solvent which is not critical for the performance of the process. Of particular interest are methylene chloride or mixtures thereof with nitromethane. Another appropriate binary system is methylene chloride/acetonitrile. The reaction of the $(OXA)_2-P-(Cl)_3$ with the organic acid salt is effected at a temperature lying between $-20°$ and $+20°$ C., with stirring over a period of time ranging from 30 to 150 minutes. A solution containing the amine, the alcohol and triethylamine or an acceptor of the released protons is added to the solution or suspension containing the activated acid.

It should also be observed that the $(OXA)_2-P-(Cl)_3$ reacts with alcohols and water in accordance with Scheme C.

SCHEME C

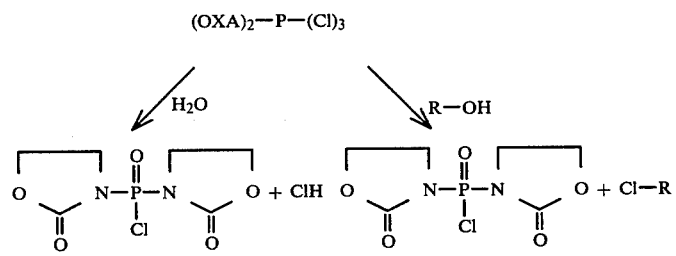

to produce N,N′-bis-(3-oxazolydinyl-2-one) chlorophosphoramide.

To facilitate the understanding of the foregoing ideas, there are described hereinafter certain examples of the practice of the invention which, in view of their purely illustrative nature, must be considered to be lacking in any limitative effect on the scope of the legal protection being applied for.

EXAMPLE I

Preparation of P-trichlorinated N,N′-bis-(3-oxazolydinyl-2-one) phosphorane 1.8 g (2 cmoles) of 2-oxazolidinone were dissolved in 20 ml of methylene chloride and 2.12 g (1 cmole) of phosphorous pentachloride were added. The mixture was stirred for 24 hours at room temperature. The mixture was degassed at reduced pressure to give the compound of the title with a quantitative yield. Thereafter methylene chloride was added up to the initial volume.

The I.R. spectrum obtained of a solution in methylene chloride shows a carbonyl band at 1780 cm$^{-1}$, without there being any reading at 1760 cm$^{-1}$ corresponding to the 2-oxazolidinone.

EXAMPLE 2

Preparation of P-trichlorinated N,N′-bis-(3-oxazolydinyl-2-one) phosphorane

Following Example 1 but replacing the methylene chloride with acetonitrile and stirring for 35 hours at room temperature, the compound of the title was obtained, also with quantitiative yield.

EXAMPLE 3

Preparation of P-trichloroinated N,N'-bis-(3-oxazolydinyl-2-one) phosphorane 1.8 g (2 cmoles) of 2-oxazolidinone were dissolved in 20 ml of nitromethane, the mixture was cooled to 0°–5° C. and the phosphorous pentachloride was added. The mixture was allowed to reach room temperature and was stirred for 30 hours. It was degassed under reduced pressure to give the compound of the title with quantitative yield.

EXAMPLE 4

Preparation of P-trichlorinated N,N'-bis-(3-oxazolydinyl-2-one) phosphorane 0.871 g (1 cmole) of 2-oxazolidinone was dissolved in 20 ml of methylene chloride and 2.12 g (1 cmole) of phosphorous pentachloride were added. A very abundant solid precipitated out in a few minutes. It was stirred for 15 minutes and 0.871 g (1 cmole) of 2-oxazolidinone was added. The mixture was held under reflux for 13 hours to give the compound of the title with a quantitative yield.

EXAMPLE 5

Preparation of P-trichlorinated N,N'-bis-(3-oxazolydinyl-2-one) phosphorane

Following Example 3 but replacing the nitromethane with a mixture of nitromethane and methylene chloride the compound of the title was obtained with a quantitative yield.

EXAMPLE 6

Preparation of P-trichlorinated N,N'-bis-(3-oxazolydinyl-2-one) phosphorane

Following Example 1 but replacing the methylene chloride with chloroform the compound of the title was obtained with a quantitative yield.

EXAMPLE 7

Benzoic acid anilide 1.8 g (2 cmoles) of 2-oxazolidinone were dissolved in 20 ml of methylene chloride and 2.12 g (1 cmole) of phosphorus pentachloride were added. The mixture was stirred at room temperature for 24 hours. It was then degassed at reduced pressure and methylene chloride then being added up to the original volume. Thereafter a solution of 1.94 g (1.6 cmoles) of benzoic acid and 2.3 ml of triethylamine in 15 ml of methylene chloride were added. The mixture was stirred at room temperature until a solution was formed. A solution of 2 ml of aniline and 2.3 ml of triethylamine in 5 ml of methylene chloride was added. The mixture was stirred at room temperature for 3½ hours. 20 ml of water were added and the pH was adjusted to approximately 1 by the addition of hydrochloric acid. The organic phase was extracted and washed twice with 20 ml of water, was dried over anhydrous sodium sulphate and dried. A crystalline pink solid was obtained. Methanol was added, partially dissolving the solid and thereafter water was added to produce an abundant crystalline solid. This was filtered, washed with methanol to give 2.8 g of benzyl anilide (yield 90%).

EXAMPLE 8

2-thienylacetic acid anilide

Following Example 7 but replacing the benzoic acid with 2-thienylacetic acid, 2.27 g (1.6 cmoles) the anilide was obtained with a 91% yield (3.185 g).

EXAMPLE 9

Tetrazolylacetic acid anilide

Following Example 7 but replacing the benzoic acid with tetrazolylacetic acid, (2.05 g) the anilide was obtained with a 92.6% yield (1.88 g).

EXAMPLE 10

Niflumic acid anilide (2-(3-trifluoromethyl-anilino)-nicotinic acid)

Following Example 7 but replacing the benzoic acid with niflumic acid, the anilide was obtained with a 92% yield, m.p.=174° C. IR spectrum, amide band at 1640 $cm^{-1}$.

EXAMPLE 11

Ethyl 1-(H)-tetrazolylacetate 1.8 g (2 cmoles) of 2-oxazolidinone were dissolved in 20 ml of methylene chloride and 2.12 g (1 cmole) of phosphorus pentachloride were added. The mixture was stirred at room temperature for 24 hours. It was degassed at reduced pressure, methylene chloride then being added up to the original volume. Thereafter a solution of 2.04 g (1.6 cmoles) of 1-(H)-tetrazolylacetic acid and 2.23 ml of triethylamine in 10 ml of methylene chloride was added. The mixture was stirred at room temperature until a solution was formed. 0.93 ml of ethanol was added and the mixture was stirred for 1 hour at room temperature. 10 ml of water were added, the organic phase was drawn off and was dried over anhydrous sodium sulphate. The solvent was driven off at reduced pressure to give 2.42 g of the ester.

Yield: 97%. IR spectrum: band at 1750 $cm^{-1}$.

EXAMPLE 12

Phenyl benzoate

Following Example 11 but replacing the 1-(H)-tetrazolylacetic acid with benzoic acid, 1.95 g (1.6 cmoles) and the ethanol with phenol, 1.51 g (1.6 cmoles) the ester of the title was obtained with a yield of 94% (2.98 g), m.p.=68°–70° C. IR spectrum: band at 1730 $cm^{-1}$.

EXAMPLE 13

Methyl 3,5-dinitrobenzoate

Following Example 11 but replacing the 1-(H)-tetrazolylacetic acid with 3,5-dinitrobenzoic acid, 3.39 g (1.6 cmoles) and the ethanol with methanol, 0.64 ml (1.6 cmoles), the ester was obtained with a yield of 96% (2.17 g), m.p.=108° C.

EXAMPLE 14

Methyl cyanacetate

Following Example 11 but replacing the 1-(H)-tetrazolylacetic acid with cyanacetic acid, 1.62 g (1.6 cmoles) and the ethanol with methanol, the ester was obtained with a yield of 91% (1.05 g), m.p.=200° C. Density: 1.0962.

EXAMPLE 15

6(3-(o-chlorophenyl)-5-methyl-4-isoxazolylcarboxyamido)penicillanic acid sodium salt 1.8 g (2 cmoles) of 2-oxazolidinone were dissolved in 20 ml of methylene chloride and 2.12 g (1 cmole) of phosphorus pentachloride were added. The mixture was stirred at room temperature for 24 hours. It was degassed at reduced pressure, methylene chloride then being added up to the original volume. Thereafter, a solution of 3.8 g (1.6 cmoles) of 3-(o-chlorophenyl)-5-methylisoxazol-4-carboxylic acid and 2.3 ml of triethylamine in 20 ml of methylene chloride was added and the mixture was stirred at room temperature almost to solution. A solution of 3.46 g (1.6 cmole) of 6-aminopenicillanic acid and 5.6 ml of triethylamine in 20 ml of methylene chloride was prepared. Once solution had been obtained, 1.3 ml of 2-ethylhexanoic acid were added to neutralise the excess triethylamine. This solution was cooled to −20° C. and the first solution of 3-(o-chlorophenyl)-5-methylisoxazol-4-carboxylic acid was added thereto dropwise. The mixture was stirred at 0°-5° C. for 3 hours. 20 ml of water were added and the pH was adjusted to approximately 1 with hydrochloric acid. The organic phase was extracted and washed twice with 20 ml of water. It was dried over anhydrous sodium sulphate. The methylene chloride was concentrated at reduced pressure to a volume of approximately 50 ml; 20 ml of methylisobutylketone were added and thereafter 12 ml of 44% sodium 2-ethylhexanoate in methylisobutylketone diluted in 12 ml of methylisobutylketone were added dropwise. 300 ml of n-hexane were added dropwise with stirring, to give an abundant precipitate. This was filtered, washed with n-hexane to give 6 g of cloxacillin sodium (78.8%).

EXAMPLE 16

6-(3-(2,6-dichlorophenyl)-5-methylisoxazolyl-4-carboxyamido)-penicillanic acid sodium salt Following Example 15 but replacing the 3-(o-chlorophenyl)-5-methylisoxazol-4-carboxylic acid with 3-(2,6-dichlorophenyl)-5-methylisoxazolyl-4-carboxylic acid, 6.6 g of dicloxacillin sodium with an 80.7% yield are obtained.

EXAMPLE 17

7-(thienylacetamido)-cephalosporanic acid 1.8 g (2 cmoles) of 2-oxazolidinone were dissolved in 20 ml of methylene chloride and 2.12 g (1 cmole) of phosphorus pentachloride were added. The mixture was stirred at room temperature for 24 hours. It was degassed at reduced pressure, methylene chloride then being added up to the original volume.

Thereafter, a solution of 2.34 g of thienylacetic acid (1.6 cmoles) and 2.3 ml of triethylamine in 20 ml of methylene chloride was added and the mixture was stirred at room temperature until almost solution. A solution of 4.84 g (1.6 cmoles, 90%) of 7-aminocephalosporanic acid and 4.96 ml (3.54 cmoles) of triethylamine in 20 ml of methylene chloride was prepared. Once solution was obtained, there was added 2.83 ml of 2-ethylhexanoic acid to neutralize the excess triethylamine. This solution was cooled to −20° C. and the first solution of thienylacetic acid was added thereto dropwise. A fair solution was produced. It was stirred at 0°-5° C. for 3½ hours. 20 ml of water were added and the pH was adjusted to approximately 1 with hydrochloric acid. A slightly turbid, pale brown organic phase was extracted. It was washed twice with 20 of water. It was dried over anhydrous sodium sulphate. The methylene chloride was concentrated at reduced pressure to a volume of approximately 50 ml; 20 ml of methylisobutylketone were added and a very abundant solid appeared. It was stirred and 12 ml of 44% sodium 2-ethylhexanoate in methylisobutylketone diluted in 12 ml of methylisobutylketone were added dropwise. 60 ml of petroleum ether were added, it was filtered and washed with petroleum ether to give 5.3 g of cephalothin sodium (79%).

EXAMPLE 18

Alpha-carboxy-5-indanyl-benzl penicillin

Following Example 15, but replacing the 3-(o-chlorophenyl)-5-methylisoxazol-4-carboxylic acid with 3.936 g (1,6 cmoles) of phenylmalonic 5-indanyl hemiester, the sodium salt of the compound of the title was prepared with an 81.2% yield (6.06 g).

EXAMPLE 19

7-cyanoacetamido cephalosporanic acid sodium salt

Following Example 15 but replacing the 3-(o-chlorophenyl)-5-methylisoxazol-4-carboxylic acid with cyanacetic acid, 1.62 g (1.6 cmoles) and the 6-aminopenicillanic acid with 7-aminocephalosporanc acid, the sodium salt of the title was obtained with an 80% yield (3.41 g).

EXAMPLE 20

6-(3-(2,6-fluorchlorophenyl)-5-methylisoxazol-4-carboxylic acid sodium salt

Following Example 15, but replacing the 3-(o-chlorophenyl)-5-methylisoxazol-4-carboxylic acid with 3-(2,6-fluorchlorophenyl)-5-methylisoxazol-4-carboxylic acid, 4.088, (1.6 cmoles), the sodium salt penicillin was obtained with an 80% yield (6.09 g).

EXAMPLE 21

D(−)phenylglycine chloride hydrochloride 5.4 g (6 cmoles) of 2-oxazolidinone were dissolved in 60 ml of acetonitrile and 6.36 g (3 cmoles) of phosphorus pentachloride were added. The mixture was stirred for 24 hours at room temperature and 3.02 (2 cmoles) of D(−)phenylglycine were added without degassing to give a suspension which was stirred at room temperature for 3 hours.

It was filtered and washed with 80 ml of acetonitrile. The solid obtained was suspended in methylene chloride to remove the remains of chlorophosphoramide. 3.87 g of chloride hydrochloride were obtained in this way.

Yield: 94%.

EXAMPLE 22

D(−)phenylglycine chloride hydrochloride 5.4 g (6 cmoles) of 2-oxazolidinone were dissolved in 60 ml of acetonitrile and 6.36 g (3 cmoles) of phosphorus pentachloride were added. The mixture was stirred for 24 hours at room temperature and was degassed at reduced pressure. 2.79 ml of dimethylacetamide were added dropwise and the mixture was stirred for 2 hours at room temperature. Thereafter 3.02 g of D(−)phenylglycine were added and the above method was followed. Yield: 90%.

EXAMPLE 23

Benzoic acid anilide 1.8 g (2 cmoles) of 2-oxazolidinone were dissolved in 20 ml of methylene chloride and 2.12 g (1 cmole) of phosphorus pentachloride were added. The mixture was stirred at room temperature for 24 hours. It was degassed at reduced pressure, methylene chloride then being added up to the original volume. It was cooled to −15° C. and 0.8 ml (1 cmole) of dimethylformamide dissolved in 5 ml of methylene chloride was added dropwise. The mixture was allowed to reach room temperature and was stirred for 1 hour, followed by the dropwise addition of a solution of 10 ml of methylene chloride, 2.1 ml of triethylamine and 1.22 g of benzoic acid. The addition was made at −10° C. and finally the mixture was stirred for 1 hour at room temperature. It was recooled to −10° C. and a solution of 10 ml of methylene chloride, 1.4 ml of triethylamine and 0.91 ml of aniline was added dropwise. From here Example 7 was followed to obtain the benzylanilide with a 95% yield.

EXAMPLE 24

2-thienylacetic acid anilide

Following Example 8 but replacing the 1.8 g of 2-oxazolidinone with 2.02 g of 4-methyl-2-oxazolidinone, the anilide was obtained with a 90% yield.

EXAMPLE 25

Phenyl benzoate

Following Example 12 but replacing the 1.8 g of 2-oxazolidinone with 2.3 g of 5-ethyl-2-oxazolidinone, the ester was obtained with a 92% yield.

EXAMPLE 26

Sodium 7-(1-(1H)-tetrazolylacetamido)-dephalosporanate 1.8 g (2 cmoles) of 2-oxazolidinone were dissolved in 20 ml of methylene chloride and 2.12 g (1 cmole) of phosphorus pentachloride was added. The mixture was stirred at 20°–25° C. for 24 hours. It was degassed at reduced pressure, methylene chloride then being added up to the original volume. Thereafter, a solution of 2.05 g (1.6 cmoles) of tetrazolylacetic acid and methylene chloride was added and the mixture was stirred at room temperature. A solution of 4.3 g (1.6 cmoles) of 7-aminocephalosporanic acid (7-ACA) dissolved in 30 ml of methylene chloride and 3.2 ml of triethylamine. It was cooled to −10° C. and the activated acid was added, it was stirred for 2 hours at 0°–5° C. to give a pale yellow solution. 50 ml of an aqueous solution at pH 7 and simultaneously 1 N NaOH to hold the pH to 8–8.1 was added. The solution was filtered and decanted. The water phase was extracted with a mixture of 70 ml of ethyl acetate and 30 ml of butanol, dropping the pH to 1.5–2. The organic extract was dried over anhydrous sodium sulphate and thereafter a solution of 20% sodium 2-ethylhexanoate in methylisobutylketone was added dropwise. The corresponding sodium cephalosporin precipitated out with a 71% yield.

When the said cephalosporin is treated under normal conditions with 1,3,4-thiadiazol-2-mercapto-5-methyl, 7-(1-(1H)-tetrazolylacetamido)-3-(5-methyl-1,3,4-thiadiazolyl-2-thiomethyl)-Δ3-cephem-4-carboxylic acid is obtained.

What we claim is:

1. A process for the activation of carboxylic acids, useful for the subsequent conversion of said carboxylic acids into their corresponding esters or amides, comprising the steps of
    (a) reacting one equivalent of a 2-oxazolidinone of the general formula

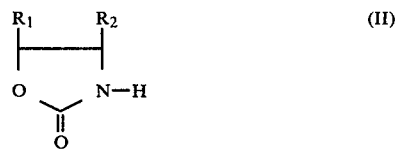

wherein $R_1$ and $R_2$ are selected from a group consisting of hydrogen and alkyl groups having from one to four carbon atoms, with a solvent with at least one half equivalent of phosphorus pentachloride at temperatures from −15° C. to +100° C. to yield P-trichlorinated N,N'-bis-3(oxazolydinyl-2-one) phosphoranes of the formula

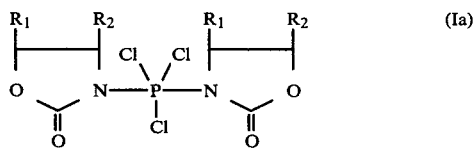

where $R_1$ and $R_2$ are likewise selected from a group consisting of hydrogen and alkyl groups having from one to four carbon atoms;
    (b) then adding a salt of the carboxylic acid to be activated, to obtain an activation reaction mixture; and
    (c) treating the resulting activation reaction mixture with one of a compound of the group comprising the compounds having an amine function and the compounds having a hydroxyl function to yield, respectively, an amide or an ester.

2. The process of claim 1, wherein $R_1$ and $R_2$ are atoms of hydrogen; the salt of the carboxylic acid to be activated is a triethylamine salt; and the amine function compound is selected from the group consisting of 6-aminopenicillanic acid, 7-aminocephalosporanic acid, 7-aminodesacetoxycephalosporanic acid, 3-substituted 7-amino-Δ3-cephem-4-carboxylic acid and their corresponding esters.

3. The process of claim 1, wherein $R_1$ and $R_2$ are atoms of hydrogen and the carboxylic acid salt is a tertiary organic base salt.

4. The process of claim 1, wherein the solvent is selected from the group consisting of methylene chloride, chloroform, nitromethane and acetonitrile either alone or in combination.

* * * * *